United States Patent [19]

Schumacher et al.

[11] Patent Number: 5,342,822
[45] Date of Patent: Aug. 30, 1994

[54] HERBICIDAL AGENTS

[75] Inventors: Hans Schumacher, Flörsheim am Main; Hans P. Huff, Eppstein/Taunus, both of Fed. Rep. of Germany

[73] Assignee: Hoechst Aktiengesellschaft, Franfurt am Main, Fed. Rep. of Germany

[21] Appl. No.: 69,132

[22] Filed: May 28, 1993

Related U.S. Application Data

[60] Division of Ser. No. 768,344, Sep. 30, 1991, Pat. No. 5,231,071, which is a continuation of Ser. No. 216,175, Jul. 7, 1988, abandoned.

[30] Foreign Application Priority Data

Jul. 10, 1987 [DE] Fed. Rep. of Germany ....... 3722801

[51] Int. Cl.$^5$ .................... A01N 43/64; A01N 43/36
[52] U.S. Cl. ..................... 504/134; 504/138
[58] Field of Search ............... 504/134, 138, 230, 284

[56] References Cited

U.S. PATENT DOCUMENTS

| | | | |
|---|---|---|---|
| 4,130,413 | 12/1978 | Handte et al. | 548/329 |
| 4,272,281 | 6/1981 | Quadranti et al. | 504/130 |
| 4,325,728 | 4/1982 | Quadranti et al. | 504/130 |
| 4,383,113 | 5/1983 | Levitt | 544/211 |
| 4,481,029 | 11/1984 | Levitt | 544/212 |
| 4,547,215 | 10/1985 | Wolf | 544/321 |
| 4,566,898 | 1/1986 | Reap | 544/211 |
| 4,601,747 | 7/1986 | Willms et al. | 544/194 |
| 4,645,526 | 2/1987 | Bauer et al. | 504/138 |
| 4,740,234 | 4/1988 | Lepone | 544/211 |

FOREIGN PATENT DOCUMENTS

| | | |
|---|---|---|
| 0007573A1 | 2/1980 | European Pat. Off. |
| 0043802A1 | 1/1982 | European Pat. Off. |
| 0131258 | 1/1985 | European Pat. Off. |
| 0157171A1 | 10/1985 | European Pat. Off. |
| 0236273A3 | 9/1987 | European Pat. Off. |
| 3536035A1 | 4/1987 | Fed. Rep. of Germany |

OTHER PUBLICATIONS

Research Disclosure, Band 262, Feb. 1986, pp. 106–107, Ref. No. 26253.
Chemical Abstracts 176829u, 97, 296 (1982).
Proceedings of the Tenth Conference of the Asian-Pacific Weed Science Society, 114–122 and 156–161 (1985).
The Pesticide Manual, 8th edition, (1987), pp. 182, 379, 404, 453, 575 and 737.
Asian–Pacific Weed Science Society, Konferenzbericht (1985), pp. 156–161.
British Crop Protection Conference Weeds (1985), 2-4, pp. 43, 2-5, 49, 2-6, 55 and 56.

*Primary Examiner*—Richard L. Raymond
*Assistant Examiner*—John D. Pak
*Attorney, Agent, or Firm*—Curtis, Morris & Safford

[57] ABSTRACT

The present invention relates to herbicidal agents which contains an effective amount of a compound of the formula I, its salt or its stereoisomers

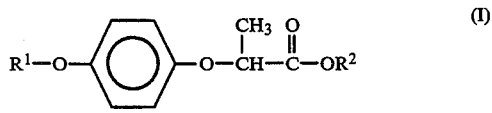

wherein
$R^1$ = a heterocyclic radical of the formulae

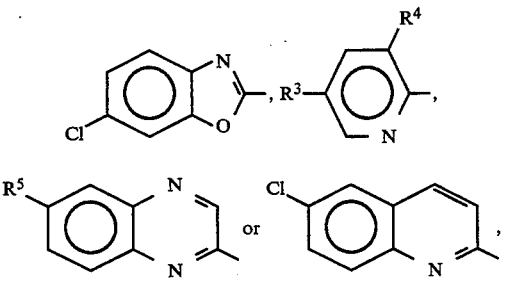

$R^2$ = H, (subst.) alkyl or ($C_2$–$C_4$)alkynyl,
$R^3$ = Cl or $CF_3$,
$R^4$ = H or Cl and
$R^5$ = F or Cl, in combination with methyl 3-[4-methoxy-6-methyl-1,3,5-triazin-2-yl)-aminocarbonyl-aminosulfonyl]-2-thiophenecarboxylate.

3 Claims, No Drawings

HERBICIDAL AGENTS

This application is division of application Ser. No. 07/768,344, filed Sep. 30, 1991, now U.S. Pat. No. 5,231,091 which in turn is a continuation of application Ser. No. 07/216,175, filed Jul. 7, 1988 now abandoned.

The present invention relates to herbicidal agents which contain an effective amount of a compound of the formula I, its salt or its stereoisomers

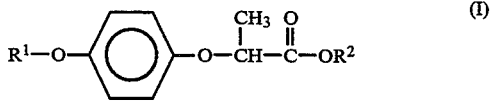

wherein
$R^1$ denotes a heterocyclic radical of the formulae

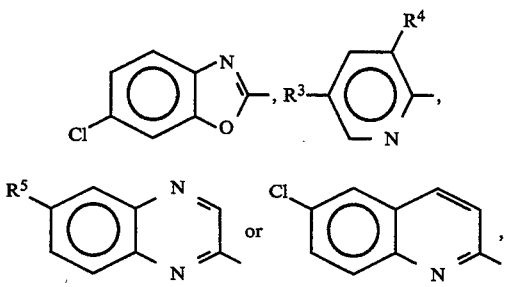

$R^2$ denotes H, $(C_1-C_4)$ alkyl which can be substituted by $(C_1-C_4)$alkoxy, or denotes $(C_2-C_4)$alkynyl,
$R^3$ denotes Cl or $CF_3$,
$R^4$ denotes H or Cl and
$R^5$ denotes F or Cl, in combination with a sulfonylurea compound of the formula II or its salt

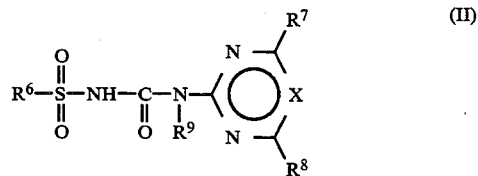

wherein

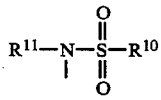

$R^6$ denotes a radical of the formula or phenyl which is substituted by $(C_1-C_4)$alkyl, halogen, halogenated $(C_1-C_4)$alkoxy or $(C_1-C_4)$alkoxycarbonyl, or thienyl which is substituted by $(C_1-C_4)$alkoxycarbonyl,
$R^7$ and $R^8$ independently of one another denote $(C_1-C_4)$alkyl or $(C_1-C_4)$alkoxy,
$R^9$ denotes $(C_1-C_4)$alkyl or hydrogen,
$R^{10}$ denotes $(C_1-C_6)$alkyl, $(C_2-C_6)$alkenyl, $(C_2-C_6)$alkynyl or $(C_1-C_6)$alkyl which is substituted by $(C_1-C_4)$alkoxy or $(C_1-C_4)$alkoxycarbonyl,
$R^{11}$ denotes H, $(C_1-C_6)$alkyl, $(C_2-C_6)$alkenyl, $(C_2-C_6)$alkynyl or cyclohexyl and X denotes CH or N.

The activities of the herbicide combinations according to the invention are remarkably high and surprisingly are considerably higher than was to be expected from the actions of the individual components.

The individual components of the formulae I and II and their use as herbicides are known.

Some compounds of the type of the formula I are described in, for example, DE-PS 3,536,035 or GB-PS 1,599,121. According to the invention, particularly important compounds of the formula I are the herbicides ethyl 2-(4-(6-chlorobenzoxazol-2-yloxy)-phenoxy)-propionate (Ia; common name: fenoxaprop-ethyl), butyl 2-(4-(5-trifluoromethyl-2-pyridyloxy)-phenoxy)propionate (Ib; common name: fluazifopbutyl) or mixtures containing an excess of the D-enantiomer of fluazifop-butyl, methyl 2-(4-(3-chloro-5-trifluoromethyl-2-pyridyloxy)phenoxy)propionate (Ic; common name: haloxyfop-methyl) and the corresponding ethoxyethyl ester (Id; common name: haloxyfop-ethoxyethyl) and ethyl 2-(4-(6-chloro-2-quinoxalyloxy)phenoxy)propionate (Ie: common name: quizalofop-ethyl), The compounds Ia to Id are described in The Pesticidal Manual, 8th edition, 1987, pp. 379, 404, 453 and 737, British Crop Protection Council.

The compounds of the formula I have an asymmetric center in the propionic acid moiety and can therefore be present as pure stereoisomers or mixtures of stereoisomers. The present invention embraces these isomers as well as their mixtures.

The compound of the formula II with $R^6$ denoting $-NR^{11}(SO_2R^{10})$ are disclosed in EP-A 0,131,258. Among these compounds, those in which $R^{10}$ and $R^{11}$ denote $(C_1-C_6)$alkyl, in particular methyl and ethyl, $R^7$ and $R^8$ denote $CH_3$ or $OCH_3$ and X denotes CH are particularly important, for example the compounds (IIa): $R^7$ and $R^8$ denote $OCH_3$, and $R^{10}$ and $R^{11}$ denote $CH_3$, or (IIb): $R^7$ and $R^8$ denote $OCH_3$, $R^{10}$ denotes $C_2H_5$, and $R^{11}$ denotes $CH_3$.

Examples of compounds of the formula II with $R^6$ denoting substituted phenyl or thienyl which may be mentioned in particular are methyl-3-[(4-methoxy-6-methyl-1,3,5-triazin-2-yl)-aminocarbonyl-aminosulfonyl]-2-thiophenecarboxylate (IIc; DPX-M 6316), methyl-2-[(4-methoxy-6-methyl-1,3,5-triazin-2-yl)-aminocarbonyl-aminosulfonyl]benzoate (IId; metsulfuron methyl), 2-chloro-N-((4-methoxy-6-methyl-1,3,5-triazin-2-yl)aminocarbonyl)benzosulfonamide (IIe; chlorosulfuron), 2-(2-chloroethoxy)-N-((4-methoxy-6-methyl-1,3,5-triazin-2-yl)aminocarbonyl)-benzosulfonamide (IIf; CGA 131,036), methyl-2-((3-(4-methoxy-6-methyl-1,3,5-triazin-2-yl)-3-methyl-aminocarbonyl-)aminosulfonyl)benzoate (IIg; DPX-L 5300), methyl-2-[(4,6-dimethoxypyrimidin2-yl)aminocarbonyl-aminosulfonylmethyl]benzoate IIh; DPX-F 5384-81). These compounds are mainly used as herbicides in cereal cultures and are known from the conference proceedings "British Crop Protection Conference-Weeds", Brighton, from the year 1985 (compound IIc: Report 1985/2- 5/p. 49; compound IIf: Report 1985/2-6/pp. 55and 56; compound IIg: Report 1985/2-4/p. 43), from the conference proceedings 1985 of the "Asians-Pacific Weed Science Society" (compound IIh: pp. 114–122 and 156–161) add from The Pesticide Manual, 8th ed. 1987, pp. 182 and 575 (compounds IId and IIe).

In the event that $R^2=H$, the compounds of the formula I can form salts. Likewise, the compounds of the formula II are capable of salt formation on a free NH group. Suitable salts of the compounds of the formulae I and II are all salts which can customarily be employed in agriculture. These include, in particular, salts of alkali metals (Na, K), salts of alkaline earth metals (Ca, Mg) and ammonium salts, it being possible for the ammonium to be monosubstituted to tetrasubstituted by radicals such as, in particular, alkyl or hydroxyalkyl.

It has now been found that the combinations according to the invention are distinguished by a surprisingly high superadditive activity, in particular in the crops wheat, rye, barley and rice.

The components of the combinations according to the invention can be mixed with each other within a relatively wide range without the high activities being lost. In general, the mixing ratios of the compounds of the formula I to the compounds of the formula II can vary from 15:1 to 1:1, in particular from 10:1 to 5:1.

With the aid of the agents according to the invention it is possible to advantageously combat numerous noxious plants in crops of useful plants such as, for example, wheat, rye, barley and rice. These noxious plants include, in particular, monocotyledon weeds such as Alopecurus myosuroides, Avena fatua or Setaria viridis, and dicotyledon weeds such as Matricaria sp., Galium aparine, Sinapis arvense or Polygonum sp.

The present invention further relates to a process for combating noxious plants in crops of useful plants, in particular in wheat, rye, barley and rice, wherein an effective amount of a compound of the formula (I) in combination with a compound of the formula (II) is applied to the crop plants or to the plantation.

The combinations according to the invention can in each case be employed in a dosage rate in the range 0.05 to 2 kg of active ingredient/ha. In particular, the application rates vary from 0.05 to 1.0 kg/ha.

The herbicidal combinations according to the invention can be applied either as tank mixes, in which the active substances are only mixed with each other immediately prior to application, or as finished formulations. As finished formulations, they may be formulated in the form of wettable powders, emulsifiable concentrates, sprayable solutions, dusting agents or granules, and they contain the customary formulation auxiliaries, such as surfactants, adhesives, dispersants, solid or liquid inert substances and grinding auxiliaries or solvents.

Wettable powders are preparations which are uniformly dispersible in water and which contain, beside the active substance(s) and in addition to a diluent or inert substance, also customary wetting agents, such as polyoxyethylated alkylphenols, polyvinyl alcohol, polyoxyethylated oleyl- or stearylamines, alkylsulfonates or alkylphenylsulfonates, and customary dispersing auxiliaries such as sodium ligninsulfonate, potassium ligninsulfonate or calcium ligninsulfonate, sodium 2,2'-binaphthyl-methane-6,6'-disulfonate and also sodium oleoylmethyltaurinate.

Emulsifiable concentrates are obtained by dissolving the active substance(s) in an organic solvent such as butanol, cyclohexanone, dimethylformamide, xylene or higher-boiling aromatics, with the addition of a non-ionic wetting agent, for example a polyoxyethylated alkylphenol, a polyoxyethylated oleyl- or stearylamine or an alkylsulfonate or alkylphenylsulfonate. Granules can be prepared either by nebulizing the active substance(s) onto adsorptive, granulated inert material, or by applying active substance concentrations onto the surface of excipients such as sand, kaolinite or granulated inert material, by means of adhesives, for example polyvinyl alcohol, sodium polyacrylate, or alternatively mineral oils.

Dusting agents are obtained by grinding the active substance with finely divided solid substances, for example talc, natural clays such as kaolin, bentonite and pyrophillite, or diatomaceous earth.

The active substances can be present in various concentrations in the commercial formulations. In wettable powders, the total concentration of active substance varies from about 20% to 90%, the remainder comprising the formulation additives indicated above. In the case of emulsifiable concentrates, the active substance concentration is about 10% to 80%.

If required, the commercial concentrates are diluted in a customary manner for application, for example, in the case of wettable powders and emulsifiable concentrates, with water.

FORMULATION EXAMPLES

Example 1

A dusting agent is obtained by mixing a) 10 pbw (pbw=parts by weight) of active substances with 90 pbw of talc or another inert substance, and comminuting the mixture in a hammer mill, or by homogenizing b) 60 pbw of active substances, 35 pbw of talc and 5 pbw of adhesive, for example a polysaccharide, in the same manner.

Example 2

A wettable powder which is readily dispersible in water is obtained by mixing 25 pbw of active substances, 64 pbw of kaolin-containing quartz as inert material, 10 pbw of potassium ligninsulfonate an d 1 pbw of sodium oleoylmethyltauride as wetting agent and dispersant, and grinding the mixture in a pinned disk mill. A formulation containing 5% active substance may have the following composition: 5% of active substances, 6% of a sulfonated naphthalene/formaldehyde condensate (for example (R)Dispersogen A of HOECHST AG), 2% of an Na salt of an alkylnaphthalenesulfonic acid (for example (R)Leonil DB of HOECHST AG), 5% of a mixture of polypropylene glycol and $SiO_2$ (for example (R)Acrotin 341 of HOECHST AG), 25% of $SiO_2$ and 57% of kaolin.

Example 3

A dispersion concentrate which is readily dispersible in water is obtained by mixing 20 pbw of active substances with 6 pbw of an alkylphenolpolyglycol ether, 3 pbw of isotridecanolpolyglycol ether (8 ethylene oxide units) and 71 pbw of paraffinic mineral oil (boiling range about 255° to above 377° C.), and grinding the mixture in a ball mill to a fineness of below 5 $\mu$pm.

Example 4

An emulsifiable concentrate is obtained from 15 pbw of active substances, 75 pbw of cyclohexanone as solvent and 10 pbw of oxyethylated nonylphenol (10 ethylene oxide units) as emulsifier.

Biological Examples

The following experiments were carried out under greenhouse conditions.

With the combinations, distinctions were made in all the cases between the calculated degree of action and that found. The calculated degree of action to be expected theory of a combination is determined with the formula according to S. R. Colby: Calculation of synergistic and antagonistic responses of herbicide combinations, Weeds 15 (1967) 20–22.

This formula reads:

$$E = X + Y - \frac{X \cdot Y}{100}$$

where

X denotes % of damage by herbicide A at an application rate of x kg/ha;

Y denotes % of damage by herbicide B at an application rate of y kg/ha;

E denotes the damage to be expected by the herbicides A+B at x+y kg/ha

If the actual damage is greater than the damage to be expected by calculation, then the action of the combination is more than additive, i.e., a synergistic effect of action is present.

Procedure of the Experiments

The test plants were grown in pots in the greenhouse. Application of the active substances in the doses indicated was carried out in each case alone or in combination (tank mixes) when the wheat (Triticum aestivum) had reached the 4–5 leaf stage and Galium aparine had reached a height of 5–10 cm.

The herbicidal action was assessed by scoring the plants 3 weeks after application. The data are based on % of damage. The results are shown in the following table, with the data in brackets corresponding to tile expected data as calculated by the Colby formula.

TABLE

| Active substance | Dose [g AS/ha] | % damage of Galium aparine | Triticum aestivum |
|---|---|---|---|
| Ia | 15 | 0 | 0 |
| | 30 | 0 | 0 |
| | 50 | 0 | 0 |
| | 75 | 0 | 0 |
| | 100 | 0 | 0 |
| | 125 | 0 | 0 |
| | 150 | 0 | 0 |
| IIa | 5 | 20 | 0 |
| | 10 | 30 | 0 |
| | 12.5 | 34 | 0 |
| | 15 | 37 | 0 |
| | 25 | 43 | 0 |
| | 50 | 70 | 0 |
| IIb | 5 | 32 | 0 |
| | 10 | 38 | 0 |
| | 12.5 | 43 | 0 |
| | 15 | 50 | 0 |
| | 25 | 63 | 0 |
| | 50 | 89 | 0 |
| IIc | 7.5 | 20 | 0 |
| | 10 | 23 | 0 |
| | 15 | 30 | 0 |
| | 20 | 35 | 0 |
| | 25 | 41 | 0 |
| | 50 | 65 | 0 |
| IId | 5 | 0 | 0 |
| | 7.5 | 0 | 0 |
| | 10 | 0 | 0 |
| | 15 | 0 | 0 |
| | 20 | 15 | 0 |
| | 25 | 20 | 0 |
| Ia + IIc | 75 + 7.5 | 50 (20) | 0 |
| | 100 + 10 | 65 (23) | 0 |

TABLE-continued

| Active substance | Dose [g AS/ha] | % damage of Galium aparine | Triticum aestivum |
|---|---|---|---|
| | 150 + 15 | 73 (30) | 0 |
| | 50 + 10 | 55 (23) | 0 |
| | 75 + 15 | 68 (30) | 0 |
| | 100 + 20 | 75 (35) | 0 |
| | 30 + 15 | 60 (30) | 0 |
| | 50 + 25 | 78 (41) | 0 |
| | 100 + 50 | 95 (65) | 0 |
| Ia + IIa | 50 + 5 | 62 (20) | 0 |
| | 100 + 10 | 82 (30) | 0 |
| | 150 + 15 | 88 (37) | 0 |
| | 50 + 10 | 83 (30) | 0 |
| | 75 + 15 | 87 (37) | 0 |
| | 125 + 25 | 95 (43) | 0 |
| | 25 + 12.5 | 75 (34) | 0 |
| | 50 + 25 | 90 (43) | 0 |
| | 100 + 50 | 100 (70) | 0 |
| Ia + IIb | 50 + 5 | 75 (32) | 0 |
| | 100 + 10 | 90 (38) | 0 |
| | 150 + 15 | 100 (50) | 0 |
| | 50 + 10 | 85 (38) | 0 |
| | 75 + 15 | 95 (50) | 0 |
| | 125 + 25 | 100 (63) | 0 |
| | 25 + 12.5 | 80 (43) | 0 |
| | 50 + 25 | 100 (63) | 0 |
| | 100 + 50 | 100 (89) | 0 |
| Ia + IId | 50 + 5 | 30 (0) | 0 |
| | 100 + 10 | 45 (0) | 0 |
| | 150 + 15 | 52 (0) | 0 |
| | 50 + 10 | 40 (0) | 0 |
| | 75 + 15 | 48 (0) | 0 |
| | 100 + 20 | 55 (15) | 0 |
| | 15 + 7.5 | 30 (0) | 0 |
| | 30 + 15 | 37 (0) | 0 |
| | 50 + 25 | 50 (20) | 0 |

[g AS] = amount of active substance in grams
Ia = ethyl 2-(4-(6-chlorobenzoazol-2-yloxy)phenoxy)-propionate
IIa = 3-(4,6-dimethoxy-2-pyrimidinyl)-1-[(N-methyl-N-methylsulfonyl)aminosulfonyl]urea
IIb = 3-(4,6-dimethoxy-2-pyrimidinyl)-1-[(N-methyl-N-ethylsulfonyl)aminosulfonyl]urea
IIc = methyl 3-[(4-methoxy-6-methyl-1,3,5-triazin-2-yl)-aminocarbonylaminosulfonyl]-2-thiophenecarboxylate
IId = methyl 2-[(4-methoxy-6-methyl-1,3,5-triazin-2-yl)-aminocarbonylaminosulfonyl]benzoate

We claim:

1. A herbicidal composition containing an effective amount of a combination of a compound of the formula I, a salt or a stereoisomer thereof,

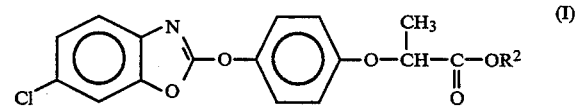

wherein $R^2$ is hydrogen or ($C_1$–$C_4$) alkyl, and a sulfonylurea compound, which is methyl 3-[4-methoxy-6-methyl-1,3,5-triazin-2-yl)-aminocarbonyl-aminosulfonyl]-2-thiophenecarboxylate, wherein said compound of formula I and said sulfonyl urea compound are in a ratio by weight of from 10:1 to 2:1.

2. The herbicidal composition as claimed in claim 1, wherein the formula I compound is ethyl 2-[4-(6-chlorobenzoxazol-2-yloxy)-phenoxy]-propionate and wherein said formula I compound and said sulfonyl urea compound are in a ratio by weight of from 10:1 to 2:1.

3. The method for combatting Galium aparine in crops of useful plants which comprises applying an effective amount of herbicidal composition as claimed in claim 2 Galium aparine plants or to the crop cultivation area.

* * * * *